United States Patent [19]

Pommer et al.

[11] Patent Number: 4,863,734

[45] Date of Patent: Sep. 5, 1989

[54] PROCESS FOR COMBATING FUNGI

[75] Inventors: Ernst-Heinrich Pommer, Limburgerhof; Maria Scherer, Godramstein; Fred Klingauf; Gabriele Herger, both of Darmstadt, all of Fed. Rep. of Germany

[73] Assignee: BASF Aktiengesellschaft, Ludwigshafen, Fed. Rep. of Germany

[21] Appl. No.: 112,955

[22] Filed: Oct. 27, 1987

[30] Foreign Application Priority Data

Sep. 17, 1987 [DE] Fed. Rep. of Germany ....... 3731239

[51] Int. Cl.$^4$ ............................................ A01N 65/00
[52] U.S. Cl. ........................................ 424/195.1; 71/3
[58] Field of Search ........................... 424/195.1; 71/3

[56] References Cited

PUBLICATIONS

Chi et al., Chem. Abs, 99, 43356g (1983).
Chi et al., Chem. Abs, 105, 139476q (1986).
Yakhak Hoeji, vol. 27, No. 1, p. 37 (1983), Chi et al., "Anthraquinones from the Rhizome of Polygonum sachalinense".

*Primary Examiner*—John W. Rollins
*Assistant Examiner*—Wendy Catchpole
*Attorney, Agent, or Firm*—Oblon, Spivak, McClelland, Maier & Neustadt

[57] ABSTRACT

Use of the plant *Reynoutria sachalinensis* for combating fungi in agriculture.

17 Claims, No Drawings

PROCESS FOR COMBATING FUNGI

The present invention relates to a process for combating fungi in agriculture by employing the plant *Reynoutria sachalinensis*.

It is known to use the rhizome of *Reynoutria sachalinensis* Nakai (=*Polygonum sachalinense*) from the Polygonaceae family as a laxative and diuretic, and for treating festering skin diseases, gonorrhea and athlete's foot (Chi et al, Yakhak Hoeji, 27, No. 1, p. 37, 1983), and to isolate, from the dried rhizome of this plant, stilbene derivatives having antibacterial and fungicidal action. It is also known that *Reynoutria sachalinensis* grows well in moderate climates, which means that this natural product can be readily produced on a large scale.

We have now found that the plant *Reynoutria sachalinensis* is excellently suited for combating fungi in agriculture. By "the plant" we mean not only the plant itself, but also plant parts such as the rhizome, stem, leaves or a blend thereof. Preferably, the dead plant, especially dried, is used. It is particularly advantageous to use the dried plant in particulate form, e.g., as granules or powder. It is particularly preferred to use the dried leaves in particulate form.

Utilizable forms of *Reynoutria sachalinensis* can be prepared in various ways, e.g., leaves or rhizome parts are air-dried or dried with the gentle application of heat, and then pulverized. The powder may for instance be extracted with an organic solvent such as ethanol, and an extract obtained after partial evaporation of the ethanol. Addition of an emulsifier and water to the extract gives a spray liquor. Aqueous extracts may also be prepared from the powder.

MANUFACTURING EXAMPLES

A. A mixture (spray liquor) suitable for preparing an aqueous liquid may be produced for example by mixing 80 parts by weight of the plant powder with 10 parts by weight of the sodium salt of a ligninsulfonic acid from a sulfite waste liquor, 3 parts by weight of the sodium salt of diisobutylnaphthalene-α-sulfonic acid and 7 parts by weight of a powdered silica gel. The mixture is triturated for example in a hammer mill. By finely distributing the mixture in water a spray liquor is obtained.

B. For an alcohol extract, 100 g of fresh plant material is coarsely comminuted and extracted with 750 ml of ethanol for 4 hours in an extraction apparatus. The crude extract obtained is evaporated to dryness in a rotary evaporator. After the addition of a small amount of acetone and an emulsifier, followed by dilution with water, a spray liquor is obtained.

C. For a cold-water extract, 10 g of plant powder is mixed with 1000 $cm^3$ of water. The mixture is allowed to stand for 24 hours, the mixture being stirred up several times. The solid components are then separated off (e.g., by filtration), and the liquid is ready for use as a spray liquor.

The plant *Reynoutria sachalinensis* has a good fungicidal action on fungi which cause damage in agriculture. The use of *Reynoutria sachalinensis* is particularly interesting for combating mildews, for example in cucurbits, ornamentals and vegetables, Botrytis cinerea in crops grown under glass, e.g., geraniums, cyclamen, cucumbers and peppers, and rusts in ornamentals.

*Reynoutria sachalinensis* and its active ingredients are well tolerated in the concentrations necessary for combating plant diseases, and make it possible for visibile plant parts to be treated.

The plant can be converted into conventional formulations such as solutions, emulsions, suspensions, powders, dusts, foams, pastes, soluble powders, granules, aerosols, suspension/emulsion concentrates, seed powders, natural and synthetic substances impregnated with the active ingredient, extremely fine encapsulation in polymeric materials, and in shell substances for seed, and into ULV fog formulations.

These formulations are prepared in conventional manner, e.g., by mixing the plant with extenders, liquid solvents, liquefied gases under pressure and/or solid carriers, with or without the use of surfactants, i.e., emulsifiers and/or dispersants and/or foams. Where water is used as extender, organic solvents, for example, may be used as auxiliary solvents. Examples of suitable liquid organic solvents are aromatics or chlorinated aliphatic hydrocarbons, such as chlorobenzene, chloroethylene and methylene chloride; aliphatic hydrocarbons, such as cyclohexane and paraffins, e.g., petroleum fractions; alcohols, such as methanol, ethanol, isopropanol, butanol and glycol, and ethers and esters thereof; ketones, such as acetone, methyl ethyl ketone, methyl isobutyl ketone and cyclohexanone; strongly polar solvents, such as dimethylformamide and dimethyl sulfoxide; and water; by liquefied gaseous extenders or carriers, such liquids are meant which are gaseous at normal temperature and atmospheric pressure, e.g., aerosol propellants such as halohydrocarbons, and butane, propane, nitrogen and carbon dioxide. Suitable solid carriers are for example natural rock flours, such as kaolins, alumina, talc, chalk, quartz, attapulgite, montmorillonite and diatomaceous earth, and synthetic rock flours, such as highly disperse silicic acid, aluminum oxide and silicates; suitable solid carriers for granules are crushed and classified natural rocks such as calcite, marble, pumice, sepiolite, dolomite, and synthetic granules made of organic material, such as sawdust, coconut shells, corn cobs and tobacco stems. Suitable surfactants, e.g., emulsifiers and/or foams, are non-ionic and anionic emulsifiers, such as polyoxyethylene fatty acid esters, polyoxyethylene fatty alcohol ethers, e.g., alkylarylpolyglycol ethers, alkyl sulfonates, alkyl sulfates, aryl sulfonates and protein hydrolysates; suitable dispersants are for example lignin sulfite waste liquors and methyl cellulose. The surfactants are employed for example in amounts of from 0.1 to 30 wt%, based on the total amount of the fungicidal agent.

The formulations may also contain spreader-stickers, such as carboxymethylcellulose, natural and synthetic powdered, granular or latex polymers, such as gum arabic, polyvinyl alcohol and polyvinyl acetate. Dyes such as inorganic pigments, e.g., iron oxide, titanium oxide, and ferrocyanine blue, and organic dyes, such as alizarin, azo, metallic phthalocyanine dyes, and trace nutrients, such as salts of iron, manganese, boron, copper, cobalt, molybdenum and zinc may be used.

Generally, the formulations contain from 0.1 to 95, and preferably from 0.5 to 90, wt% of the plant or plant extract.

In the formulations or the various application forms the plant may be mixed with other, prior art, active ingredients, such as bactericides, insecticides, acaricides, nematocides, herbicides, agents for preventing damage by birds, growth regulators, plant nutrients, soil structure ameliorants, and fungicides, e.g., sulfur (wettable), sodium bicarbonate ($NaHCO_3$), and lecithin.

The plant may be used as such, in the form of formulations or application forms prepared from them by further dilution, such as ready-to-use solutions, emulsions, suspensions, powders, pastes and granules. Application is in the conventional manner, e.g., by watering, impregnation, spraying, sprinkling, atomizing, evaporating, injecting, slurrying, painting, dusting and scattering.

For the treatment of plant parts, the plant concentrations in the application forms may vary within a wide range, but are generally from 2 to 0.1, and preferably from 1 to 0.5, wt%.

The application rates depend on the effect desired, and range from 2 to 20 kg of the plant per hectare. The following examples illustrate the good fungicidal action of the plant.

USE EXAMPLE 1

Action on *Plasmopara viticola*

Leaves of potted vines of the Müller-Thurgau variety were sprayed with aqueous spray liquors. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

Assessment of the leaf surface area attacked in % of the total leaf area

| Formulation type | Leaf attack in % after treatment with a 1% plant powder formulation (wt %) |
|---|---|
| Wettable powder | 16 |
| Alcohol extract | 7 |
| Cold-water extract (24 hours) | 8 |
| Control (untreated) | 86 |

USE EXAMPLE 2

Action on wheat mildew

Leaves of pot-grown wheat seedlings of the "Frühgold" variety were sprayed with aqueous spray liquors, and dusted, 24 hours after the sprayed-on layer had dried, with spores of wheat mildew (*Erysiphe graminis* var. tritici). The test plants were then set up in the greenhouse at 20° to 22° C. and a relative humidity of 75 to 80%. The extent of mildew spread was determined after 7 days.

Assessment of the leaf surface area attacked in % of the total leaf area

| Formulation type | Leaf attack after treatment with a 1 wt % plant powder formulation |
|---|---|
| Wettable powder | 8 |
| Alcohol extract | 12 |
| Cold-water extract (24 hours) | 25 |
| Control (untreated) | 81 |

USE EXAMPLE 3

Action on cucumber mildew

Leaves of young cucumber seedlings of the "Chinesische Schlange" variety were sprayed, at the two-leaf stage, with aqueous conidial suspensions of cucumber mildew (*Erysiphe cichoracearum* and *Sphaerotheca fuliginea*). After one day, these plants were sprayed to runoff with aqueous spray liquors, and set up in the greenhouse at from 20° to 22° C. and a relative humidity of 70 to 80%. The extent of fungus attack was assessed 21 days after inoculation.

Assessment of the leaf surface area attacked in % of the total leaf area

| Formulation type | Leaf attack after treatment with a 1 wt % plant powder formulation |
|---|---|
| Wettable powder | 8 |
| Alcohol extract | 0.7 |
| Cold-water extract (24 hours) | 8 |
| Control (untreated) | 86 |

USE EXAMPLE 4

Action on *Botrytis cinerea* in peppers

Pepper seedlings of the "Neusiedler Ideal Elite" variety were sprayed, after 4 to 5 leaves were well developed, to runoff with aqueous spray liquors. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

Assessment of the leaf surface area attacked in % of the total leaf area

| Formulation type | Leaf attack after treatment with a 1 wt % plant powder formulation |
|---|---|
| Wettable powder | 18 |
| Alcohol extract | 42 |
| Cold-water extract (24 hours) | 10 |
| Control (untreated) | 70 |

USE EXAMPLE 5

Action on bean rust

Leaves of pot-grown bean plants of the "Fogi" variety were artificially inoculated with spores of *Uromyces appendiculatus* (bean rust) and placed for 24 hours in a water vapor-saturated chamber at 22°–24° C. The plants were then sprayed to runoff with aqueous spray liquors, and left in the greenhouse at from 22° to 25° C. and a relative humidity of 70 to 80%. The extent of fungus spread was determined after 8 days.

Assessment of the leaf surface area attacked in % of the total leaf area

| Formulation type | Leaf attack after treatment with a 1 wt % plant powder formulation |
|---|---|
| Wettable powder | 10 |
| Alcohol extract | 10 |
| Cold-water extract (24 hours) | 10 |
| Control (untreated) | 90 |

We claim:

1. A fungicidal composition for use in agriculture, consisting of the leaves of the plant *Reynoutria sachalinensis* in a fungicidally effective amount, and a surfactant.

2. The fungicidal composition of claim 1, wherein the leaves are in a dry particulate form.

3. The fungicidal composition of claim 1, in admixture with water.

4. A fungicidal composition for use in agriculture, consisting of the leaves of the plant *Reynoutria sachalinensis* in a dry particulate form.

5. A fungicidal composition for use in agriculture, consisting of the leaves of the plant *Reynoutria sachalinensis* in a particulate form in admixture with water, the plant being present in a fungicidally effective amount.

6. A process for combating fungi in agriculture, wherein the fungi or the plant parts to be protected against fungus attack are treated with a fungicidally effective amount of the leaves of the plant *Reynoutria sachalinensis*.

7. The process of claim 6, wherein the leaves of the plant are in a dry particulate form.

8. The process of claim 6, wherein the leaves of the plant are in a particulate form in admixture with water.

9. The process of claim 6, wherein the leaves of the plant are in a particulate form in admixture with a surfactant.

10. The process of claim 9, wherein the leaves of the plant are in admixture with water and a surfactant.

11. A fungicidal composition for use in agriculture, consisting of the leaves and stems of the plant *Reynoutria sachalinensis* in a fungicidally effective amount, and a surfactant.

12. A fungicidal composition for use in agriculture, consisting of the leaves and stems of the plant *Reynoutria sachalinensis* in a dry particulate form.

13. A fungicidal composition for use in agriculture, consisting of the leaves and stems of the plant *Reynoutria sachalinensis* in a particulate form in admixture with water, the plant being present in a fungicidally effective amount.

14. A process for combatting fungi in agriculture, wherein the fungi or the plant parts to be protected against fungus attack are treated with a fungicidally effective amount of the leaves and stems of the plant *Reynoutria sachalinensis*.

15. The process of claim 14, wherein the leaves and stems of the plant are in a dry particulate form.

16. The process of claim 14, wherein the leaves and stems of the plant are in a particulate form in admixture with water.

17. The process of claim 14, wherein the leaves and stems of the plant are in a particulate form in admixture with a surfactant.

* * * * *